(12) United States Patent
Irisawa

(10) Patent No.: US 11,445,916 B2
(45) Date of Patent: Sep. 20, 2022

(54) INSERT, OPTICAL INSERT, AND PHOTOACOUSTIC MEASUREMENT DEVICE

(71) Applicant: FUJIFILM CORPORATION, Tokyo (JP)

(72) Inventor: Kaku Irisawa, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 419 days.

(21) Appl. No.: 16/816,254

(22) Filed: Mar. 12, 2020

(65) Prior Publication Data

US 2020/0260961 A1 Aug. 20, 2020

(30) Foreign Application Priority Data

Sep. 15, 2017 (JP) .............................. JP2017-177887

(51) Int. Cl.
| | | |
|---|---|---|
| A61B 5/00 | (2006.01) | |
| G01N 21/17 | (2006.01) | |
| A61B 8/00 | (2006.01) | |
| A61B 17/34 | (2006.01) | |
| A61B 8/08 | (2006.01) | |

(52) U.S. Cl.
CPC .......... *A61B 5/0095* (2013.01); *A61B 5/0035* (2013.01); *A61B 5/6843* (2013.01);
(Continued)

(58) Field of Classification Search
None
See application file for complete search history.

(56) References Cited

U.S. PATENT DOCUMENTS 5,725,514 A * 3/1998 Grinblat .................. A61F 9/007
604/117
6,224,566 B1 * 5/2001 Loeb ................. A61M 25/0662
604/20
(Continued)

FOREIGN PATENT DOCUMENTS

JP 2016-187484 A 11/2016
WO 2014/109148 A1 7/2014
(Continued)

OTHER PUBLICATIONS

International Search Report issued in International Application No. PCT/JP2018/018014 dated Jul. 24, 2018.
(Continued)

*Primary Examiner* — Dominic J Bologna
(74) *Attorney, Agent, or Firm* — Solaris Intellectual Property Group, PLLC

(57) ABSTRACT

An insert according to the invention includes a needle tube that has an inclined surface having a leading end opening, a needle base that has a chamber communicating with an inside of the needle tube and holds the needle tube, and a light introduction portion that communicates with the chamber and has an insertion path into which a light guide member is inserted. In a case in which the light guide member is inserted into the insertion path, is constrained at a first constraint point, becomes free, is bent, is constrained at a second constraint point, and is inserted into the needle tube and a point where an extension line in an insertion direction of the light guide member in the vicinity of a chamber-side opening in the insertion path intersects a line which passes through the second constraint point and is parallel to an axial direction of the needle tube is an intersection point, a distance between the intersection point
(Continued)

and the second constraint point is longer than a distance between the first constraint point and the intersection point.

12 Claims, 10 Drawing Sheets

(52) U.S. Cl.
CPC .......... *A61B 5/6848* (2013.01); *A61B 8/4416* (2013.01); *A61B 8/5246* (2013.01); *A61B 17/3403* (2013.01); *G01N 21/1702* (2013.01); *A61B 8/4444* (2013.01); *A61B 2017/3413* (2013.01); *G01N 2201/06113* (2013.01); *G01N 2201/08* (2013.01)

(56) References Cited

U.S. PATENT DOCUMENTS

| | | | |
|---|---|---|---|
| 2014/0121538 A1* | 5/2014 | Hendriks | A61B 5/6848 600/478 |
| 2017/0112386 A1* | 4/2017 | Irisawa | A61B 8/5246 |
| 2017/0139155 A1* | 5/2017 | Tong | G02B 6/3821 |
| 2018/0028117 A1 | 2/2018 | Desjardins et al. | |
| 2018/0116630 A1* | 5/2018 | Dykes | A61B 8/12 |

FOREIGN PATENT DOCUMENTS

| | | |
|---|---|---|
| WO | 2016/006188 A1 | 1/2016 |
| WO | 2016/113543 A1 | 7/2016 |
| WO | 2017/090248 A1 | 6/2017 |
| WO | 2017/130805 A1 | 8/2017 |

OTHER PUBLICATIONS

Written Opinion of the ISA issued in International Application No. PCT/JP2018/018014 dated Jul. 24, 2018.

* cited by examiner

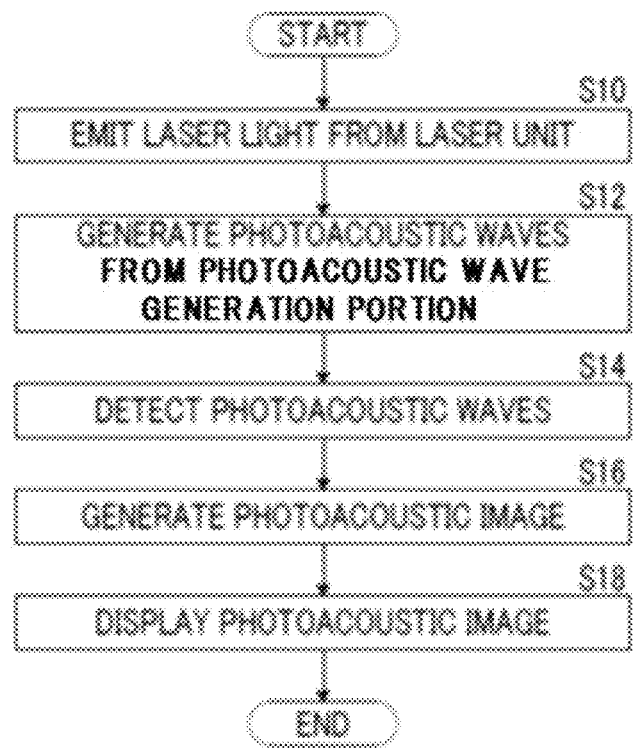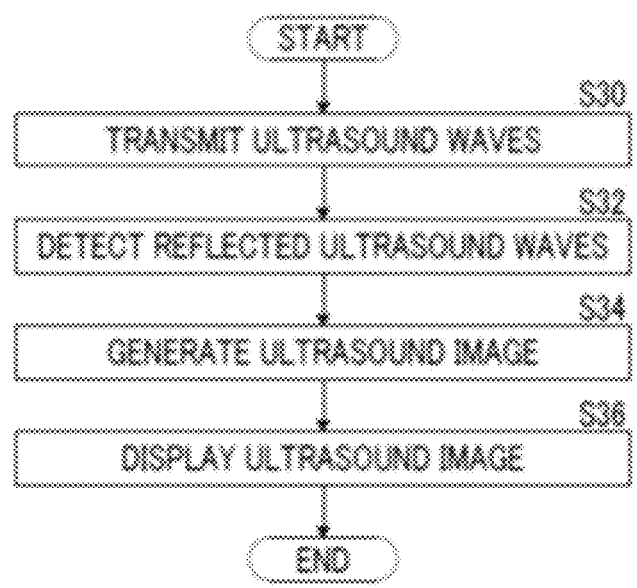

INSERT, OPTICAL INSERT, AND PHOTOACOUSTIC MEASUREMENT DEVICE

CROSS-REFERENCE TO RELATED APPLICATIONS

This application is a continuation application of International Application No. PCT/JP2018/018014, filed May 9, 2018, the disclosure of which is incorporated herein by reference in its entirety. Further, this application claims priority from Japanese Patent Application No. 2017-177887, filed Sep. 15, 2017, the disclosure of which is incorporated herein by reference in its entirety.

BACKGROUND OF THE INVENTION

1. Field of the Invention

The present invention relates to an insert of which at least a portion is inserted into a subject, an optical insert comprising the insert and a light guide member, and a photoacoustic measurement device comprising the optical insert.

2. Description of the Related Art

In recent years, photoacoustic imaging (PAI) has been known which captures an image of the inside of a living body using a photoacoustic effect. In general, in photoacoustic imaging, the inside of a living body is irradiated with pulsed laser light and living tissues absorb the energy of the pulsed laser light the living body. As a result, photoacoustic waves which are elastic waves are generated in the living body. The photoacoustic waves are detected by, for example, an ultrasound probe. A photoacoustic image is formed on the basis of a detection signal. In this way, it is possible to visualize the inside of the living body on the basis of the photoacoustic waves. In addition, for the photoacoustic imaging, WO2014/109148A, WO2016/006188A, and JP2016-187484A disclose a technique that can check the position of a leading end of a puncture needle using the photoacoustic imaging. In this technique, a light guide member, such as an optical fiber, is provided in a puncture needle so as to reach the vicinity of the leading end of the puncture needle, a light absorber that covers a leading end of the light guide member is provided such that light propagated through the light guide member is incident on the light absorber from the leading end of the light guide member. In a case in which various treatments are performed using this puncture needle, light is incident on the light absorber from the leading end of the light guide member to generate photoacoustic waves from the light absorber and the photoacoustic waves are detected. Then, an acoustic image of the light absorber is displayed such that the leading end of the light guide member, that is, the leading end of the puncture needle can be checked. In the photoacoustic image, the photoacoustic wave generation portion appears as a bright point. Therefore, the use of the photoacoustic image makes it possible to check the position of the puncture needle.

Some puncture needles used in the photoacoustic imaging comprise a needle tube that has an inclined surface having a leading end opening at the leading end, a needle base that has a chamber whose leading end communicates with the needle tube and holds a rear end portion of the needle tube, and a light introduction portion that communicates with the chamber and has an insertion path which obliquely extends backward from the chamber in the downward direction and into which an optical fiber is inserted from the lower side. In a case in which the inclined surface having the leading end opening formed therein is disposed so as to face downward in the puncture needle, the upper inner surface of the needle tube is a long inner surface that is located on the leading end side of the needle tube and the lower inner surface of the needle tube is a short inner surface. The light guide member is pressed against the long inner surface, that is, the upper inner surface of the needle tube to prevent the light guide member from protruding from the leading end opening, that is, the short inner surface.

SUMMARY OF THE INVENTION

However, in the puncture needle, in a case in which the inclined surface having the leading end opening is disposed so as to face upward, the upper inner surface of the needle tube is a short inner surface and the lower inner surface of the needle tube is a long inner surface. As described above, in a case in which the light guide member is pressed against the upper inner surface, there is a concern that the light guide member will protrude from the leading end opening, that is, the short inner surface. In addition, it is preferable that the leading end of the light guide member is disposed close to the leading end of the needle tube. Therefore, it is desirable that the light guide member is fixed to the long inner surface. However, in a case in which the light guide member is pressed against the short inner surface, it is difficult to fix the light guide member to the long inner surface of the puncture needle.

The invention has been made in view of the above-mentioned problems and an object of the invention is to provide an insert, an optical insert, and a photoacoustic measurement device in which a light guide member is easily fixed to an inner surface of a leading end of a needle tube of a puncture needle.

According to the invention, there is provided an insert of which at least a portion is inserted into a subject. The insert comprises: a hollow needle tube that has an inclined surface comprising a leading end opening at a leading end; a long needle base that has a chamber whose leading end communicates with an inside of the needle tube and holds a rear end portion of the needle tube; and a light introduction portion that communicates with the chamber and has an insertion path into which a light guide member guiding light emitted from a light source is inserted. In a cross section including an axis of the needle tube and an axis of the insertion path, in a case in which a direction from the axis of the needle tube to a side on which the light introduction portion is located is a downward direction and a direction opposite to the downward direction is an upward direction, the inclined surface faces upward, a chamber-side opening of the insertion path is formed in a lower wall of the chamber, and the insertion path obliquely extends backward from the chamber-side opening in the downward direction. An upper wall of the chamber which is on a leading end side from the chamber-side opening is formed such that a height thereof gradually increases from the leading end to a rear end. In a case in which the light guide member is inserted into the insertion path, is constrained at a first constraint point Y, becomes free, is bent, is constrained at a second constraint point X, and is inserted into the needle tube and a point where an extension line in an insertion direction of the light guide member in the vicinity of the chamber-side opening in the insertion path intersects a line which passes through the second constraint point X and is parallel to an axial direction of the needle tube is an intersection point A, a distance a between the intersection point A and the second constraint point X is longer than a distance b between the first constraint point Y and the intersection point A.

In the invention, in a main body formed by connecting the needle tube and the needle base, the leading end side of the needle tube is referred to as a leading end side and a side opposite to the leading end side is referred to as a rear end side. The term "the insertion path obliquely extending backward in the downward direction" means that the insertion path extends to the rear end below the chamber so as to be inclined with respect to the chamber.

In the invention, the "constraint" includes not only that a component is completely fixed, but also that at least a portion of the component comes into contact with the light guide member to prevent the movement of the light guide member in any direction. That is, the "constraint" means that the component is not moved in a completely free state.

In the invention, the "height gradually increasing from the leading end to the rear end" means that there is a difference in the height of the upper wall of the chamber. That is, this means that the distance from the upper wall of the chamber to the axis of the needle tube increases from the leading end to the rear end.

In the invention, the "extension line in the insertion direction of the light guide member" means an extension line in the insertion direction in the vicinity of the chamber-side opening of the insertion path and the "the insertion direction in the vicinity of the chamber-side opening" means an insertion direction that includes at least the chamber-side opening and has a length where the insertion direction of the light guide member is determined.

In the insert according to the invention, in the cross section including the axis of the needle tube and the axis of the insertion path, a lower wall of the chamber which is one the leading end side from the chamber-side opening may have a shape that extends from the chamber-side opening along an extension line of a lower wall of the insertion path and is bent below the extension line and a distance from a bent point where the lower wall is bent to the axis of the needle tube may be shorter than a distance from the upper wall of the chamber to the axis of the needle tube on a line orthogonal to the axis of the needle tube at the bent point.

In the insert according to the invention, in the cross section including the axis of the needle tube and the axis of the insertion path, the lower wall of the chamber which is on the leading end side from the chamber-side opening may be formed with the same height as a lower surface of a hollow portion of the needle tube through the bent point.

In the insert according to the invention, in the cross section including the axis of the needle tube and the axis of the insertion path, the upper wall of the chamber which is on the leading end side from the intersection point A may be formed such that a height thereof gradually increases from a height position of an upper surface of the hollow portion of the needle tube to the rear.

According to the invention, there is provided an optical insert comprising: the insert according to the invention; the light guide member that is inserted into the insertion path, is constrained at the first constraint point Y, becomes free, is bent, is constrained at the second constraint point X, and is inserted into the needle tube.

In the optical insert according to the invention, a clearance between an inside diameter of a chamber-side portion of the insertion path and an outside diameter of the light guide member may be equal to or less than 0.5 mm.

In the invention, the clearance means the sum of the gaps between the insertion path and the light guide member in a direction orthogonal to the axial direction of the light guide member at the position where the inside diameter of the insertion path is the minimum.

In the optical insert according to the invention, the light guide member may be fixed in the insertion path by an adhesive.

The optical insert according to the invention may further comprise a protective tube that covers the light guide member. The light guide member may be fixed in the protective tube by an adhesive.

The optical insert according to the invention may further comprise a photoacoustic wave generation portion that is provided at a light emission end of the light guide member which is disposed on the leading end side of the needle tube, absorbs light emitted from the light emission end, and generates photoacoustic waves.

In the optical insert according to the invention, the photoacoustic wave generation portion may be made of an ultraviolet-curable resin including a pigment that absorbs light guided by the light guide member.

In the optical insert according to the invention, the ultraviolet-curable resin may function as an adhesive that fixes the photoacoustic wave generation portion to the needle tube.

According to the invention, there is provided a photoacoustic measurement device comprising: the optical insert according to the invention; a light source unit that emits light which is absorbed by the photoacoustic wave generation portion of the optical insert; and an acoustic wave detection unit that detects photoacoustic waves generated from the photoacoustic wave generation portion.

According to the invention, there is provided an insert of which at least a portion is inserted into a subject. The insert comprises: a hollow needle tube that has an inclined surface comprising a leading end opening at a leading end; a long needle base that has a chamber whose leading end communicates with an inside of the needle tube and holds a rear end portion of the needle tube; and a light introduction portion that communicates with the chamber and has an insertion path into which a light guide member guiding light emitted from a light source is inserted. In a cross section including an axis of the needle tube and an axis of the insertion path, in a case in which a direction from the axis of the needle tube to a side on which the light introduction portion is located is a downward direction and a direction opposite to the downward direction is an upward direction, the inclined surface faces upward, a chamber-side opening of the insertion path is formed in a lower wall of the chamber, and the insertion path obliquely extends backward from the chamber-side opening in the downward direction. An upper wall of the chamber which is on the leading end side from the chamber-side opening is formed such that a height thereof gradually increases from the leading end to a rear end. In a case in which the light guide member is inserted into the insertion path, is constrained at a first constraint point Y, becomes free, is bent, is constrained at a second constraint point X, and is inserted into the needle tube and a point where an extension line in an insertion direction of the light guide member in the vicinity of the chamber-side opening in the insertion path intersects a line which passes through the second constraint point X and is parallel to an axial direction of the needle tube is an intersection point A, a distance a between the intersection point A and the second constraint point X is longer than a distance b between the first constraint point Y and the intersection point A. In this configuration, the force that makes the distance a equal to the distance b acts due to the straightening force of the light guide member. The trajectory of the light guide member is bent before the intersection point A on an extension line in the insertion direction of the light guide member in the insertion path. Therefore, the light guide member is inclined from the upper side to the lower side between the intersection point A and the second constraint point and is pressed against an inner surface on the side opposite to the side where the leading end opening is located in the needle tube. As a result, it is easy to fix the light guide member to the inner surface of the leading end of the needle tube of, for example, the puncture needle.

BRIEF DESCRIPTION OF THE DRAWINGS

FIG. 3 is a flowchart illustrating a photoacoustic image generation process.

FIG. 4 is a flowchart illustrating an ultrasound image generation process.

DESCRIPTION OF THE PREFERRED EMBODIMENTS

Figure 1:
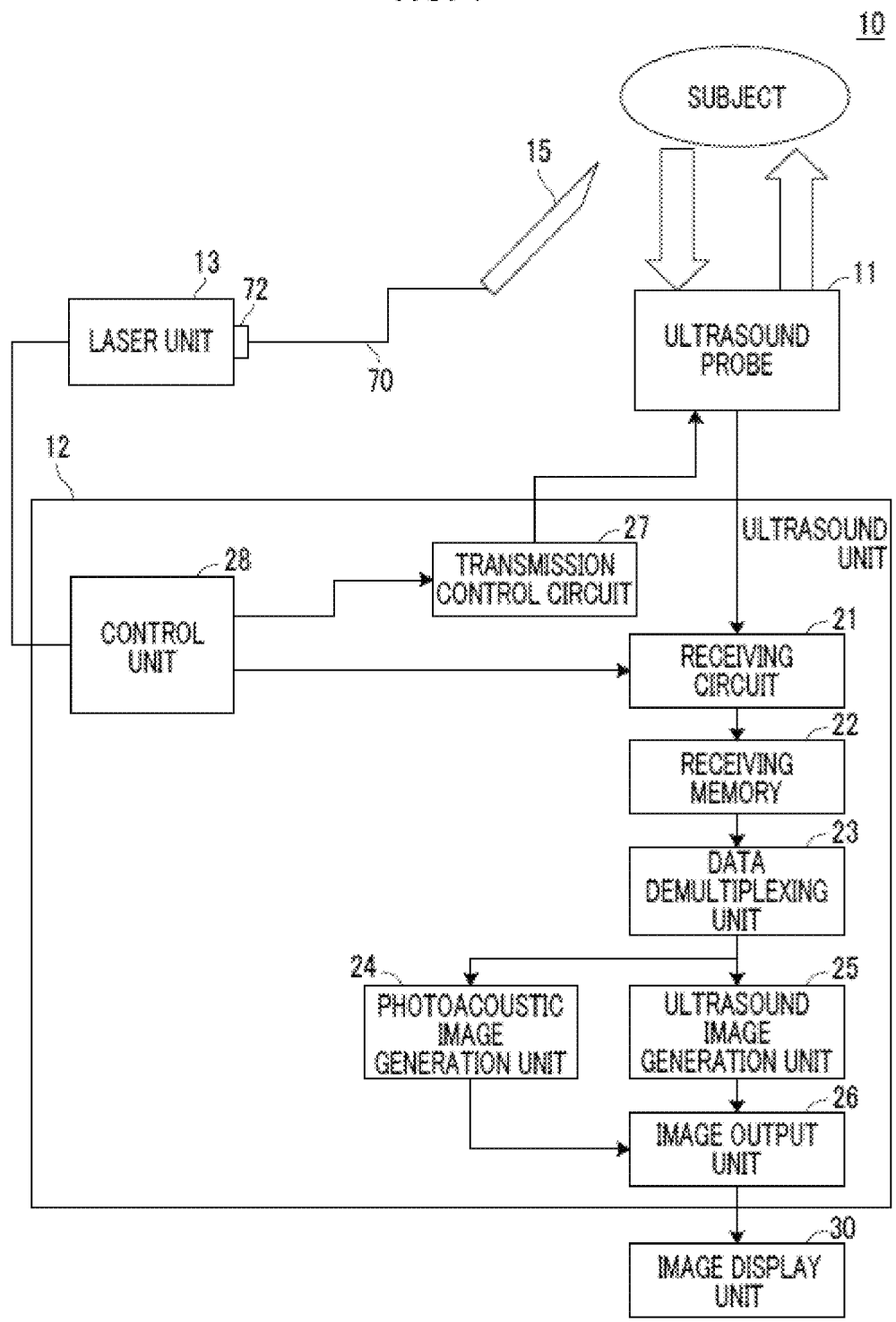
FIG. 1 is a block diagram schematically illustrating the configuration of a photoacoustic measurement device comprising a puncture needle using a first embodiment of an insert according to the invention.

Hereinafter, a photoacoustic measurement device 10 comprising a puncture needle using a first embodiment of an optical insert according to the invention will be described in detail with reference to the drawings. The photoacoustic measurement device 10 according to this embodiment is characterized by the configuration of the puncture needle. First, the overall configuration of the photoacoustic measurement device 10 will be described. FIG. 1 is a diagram schematically illustrating the configuration of the photoacoustic measurement device 10 according to this embodiment.

As illustrated in FIG. 1, the photoacoustic measurement device 10 according to this embodiment comprises an ultrasound probe 11, an ultrasound unit 12, a laser unit 13, and a puncture needle 15. The puncture needle 15 and the laser unit 13 are connected by an optical cable 70 having an optical fiber. The optical cable 70 includes a portion extending from an optical fiber 18 in the puncture needle 15, which will be described below, and has an end at which a connector 72 is provided. The laser unit 13 is connected to the connector 72. The puncture needle 15 and the optical cable 70 are disposable. In addition, in this embodiment, ultrasonic waves are used as acoustic waves. However, the invention is not limited to the ultrasonic waves. Acoustic waves with an audible frequency may be used as long as an appropriate frequency can be selected according to, for example, an inspection target or measurement conditions. In addition, for example, a syringe or a transfusion tube is connected to the puncture needle 15 and can be used to inject a liquid medicine, which is not illustrated in FIG. 1.

The laser unit 13 corresponds to a light source unit according to the invention and comprises, for example, a semiconductor laser light source. Laser light emitted from a laser diode light source of the laser unit 13 is guided by the optical cable 70 and is incident on the puncture needle 15. The laser unit 13 according to this embodiment emits pulsed laser light in a near-infrared wavelength range. The near-infrared wavelength range means a wavelength range of about 700 nm to 2000 nm. In this embodiment, the laser diode light source is used. However, other laser light sources, such as a solid-state laser light source, a fiber laser light source, and a gas laser light source, may be used or, for example, a light emitting diode light source other than the laser light source may be used.

Figure 2:
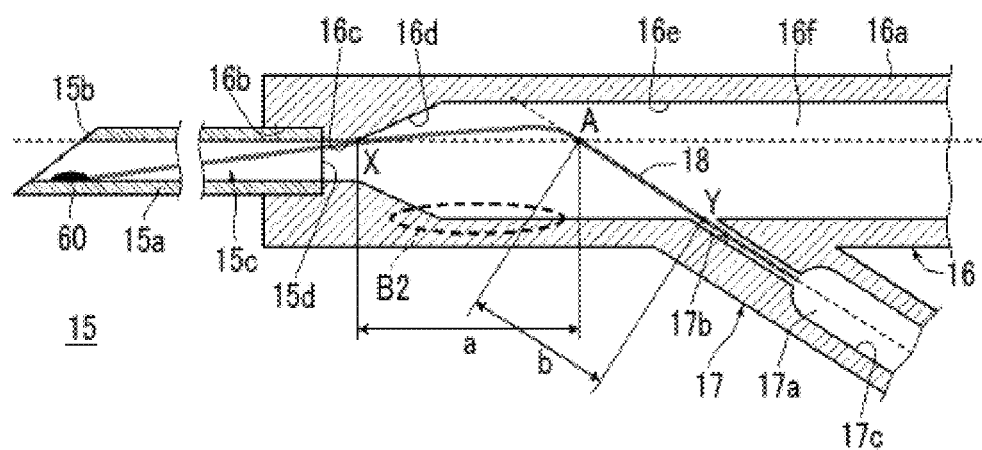
FIG. 2 is a cross-sectional view illustrating the configuration of a leading end portion of the puncture needle according to the first embodiment.

The puncture needle 15 is an embodiment of the optical insert according to the invention and is a needle of which at least a portion is inserted into a subject. The insert according to the embodiment of the invention corresponds to an optical insert, that is, a portion formed by excluding the optical fiber 18 which will be described below from the puncture needle 15. FIG. 2 is a cross-sectional view illustrating the configuration of the vicinity of a leading end of the puncture needle 15 in which the optical fiber 18 is provided. FIG. 2 illustrates a cross section including the axis of a needle tube 15a and the axis of an insertion path 17a in the puncture needle 15. In FIG. 2, the length of the needle tube 15a is exaggerated and is less than the actual length of the needle tube for convenience. In the following description, the side on which the needle tube 15a is disposed is referred to as a leading end and the side on which a needle base 16 is disposed is referred to as a rear end in FIG. 2. In addition, the side on which a light introduction portion 17 is disposed is referred to as a lower side, that is, the lower side of paper is referred to as a lower side.

As illustrated in FIG. 2, the puncture needle 15 comprises the needle tube 15a, the needle base 16, the light introduction portion 17, the optical fiber 18, and a photoacoustic wave generation portion 60. In this embodiment, the optical fiber 18 corresponds to a light guide member according to the invention.

The needle tube 15a is made of, for example, metal, has a leading end opening 15b at the leading end, and is formed in a hollow shape. The leading end of the needle tube 15a is formed obliquely with respect to the axis of the needle tube 15a such that the side on which the light introduction portion 17, which will be described below, is located, that is, a lower side is long and a side opposite to the side on which the light introduction portion 17 is located, that is, an upper side is short. The leading end opening 15b is provided in an inclined surface that is obliquely formed. The leading end opening 15b faces upward. The diameter (inside diameter) of a hollow portion 15c of the needle tube 15a may be large enough to provide the optical fiber 18 which will be described below and is, for example, equal to or greater than 0.13 mm and equal to or less than 2.64 mm. The diameter (inside diameter) of the hollow portion 15c of the needle tube 15a depends on the outside diameter of the optical fiber 18 and is preferably equal to or greater than 0.26 mm in order to easily provide the optical fiber 18. The needle tube 15a is inserted into the subject from the leading end opening 15b during injection.

The needle base 16 includes a needle base main body 16a having a long and hollow shape, an anterior end portion 16b which accommodates and holds a rear end portion 15d of the needle tube 15a, a first chamber 16c which has an inside diameter which is equal to or slightly smaller than the inside diameter of the needle tube 15a and extends backward along the axis, a second chamber 16d which communicates with the first chamber 16c and whose diameter increases toward the rear, and a third chamber 16e which communicates with the second chamber 16d and extends backward along the axis. The first chamber 16c, the second chamber 16d, and the third chamber 16e form a chamber 16f of the needle base 16.

In the chamber 16f, the first chamber 16c communicates with the hollow portion 15c of the needle tube 15a and the rear end of the third chamber 16e is connected to a syringe or a liquid feeding tube (not illustrated) and has a liquid inlet for receiving, for example, liquid medicines. The chamber 16f is formed such that the inside diameter of the first chamber 16c is less than the inside diameter of the second chamber and the inside diameter of the third chamber. That is, the height of the upper wall of the chamber 16f on the leading end side from a chamber-side opening of the insertion path 17a which will be described below increases from the leading end to the rear end. For example, in the cross-sectional view of FIG. 2, in a case in which the inside diameter of the needle tube 15a is 1 mm and the inside diameter of the third chamber 16e is 2 mm, the distance from the upper inner surface of the hollow portion 15c of the needle tube 15a to the upper inner surface of the third chamber 16e is 0.5 mm.

The light introduction portion 17 is obliquely connected to the needle base 16 and is formed in a linear tube shape that is obliquely branched from the needle base 16 to the rear. The light introduction portion 17 comprises the insertion path 17a into which the optical fiber 18 is inserted and the insertion path 17a includes an outlet path 17b that communicates with the third chamber 16e and an inlet path 17c that communicates with the outlet path 17b and has a larger diameter than the outlet path 17b. Since the outlet path 17b is formed with a smaller diameter than the inlet path 17c, it is possible to define the insertion direction of the optical fiber 18 in the insertion path 17a. That is, the axial direction of the outlet path 17b is matched with the insertion direction of the optical fiber 18. Since the inside diameter of the outlet path 17b is larger than the outside diameter of the optical fiber 18, the term "match" means that the directions are not exactly matched with each other, but have a slight clearance therebetween. Here, the clearance is the sum of the gaps between the optical fiber 18 and the outlet path 17b in a direction orthogonal to the axial direction of the outlet path 17b. In the invention, it is preferable that the clearance is equal to or less than 0.5 mm in order to define the insertion direction of the optical fiber 18. In addition, for example, at least the side of the outlet path 17b which is close to the chamber 16f is closed with an adhesive after the optical fiber 18 is inserted in order to prevent the inflow of liquid medicines from the chamber 16f.

The inlet path 17c of the insertion path 17a can be formed with a larger size than the outlet path 17b in order to interpose, for example, a protective tube 20 (which will be described below) for covering the optical fiber 18 or a bush that does not break even in a case in which it is bent.

The optical fiber 18 is laid in the puncture needle 15 and is provided in the hollow portion 15c of the needle tube 15a along the length direction of the needle tube 15a. The photoacoustic wave generation portion 60 is provided at the leading end (light emission end) of the optical fiber 18 which is on the leading end side of the needle tube 15a so as to cover a leading end portion of the optical fiber 18. Then, light guided by the optical fiber 18 in the optical cable 70 is emitted from the light emission end of the optical fiber 18 to the photoacoustic wave generation portion 60.

As described above, the photoacoustic wave generation portion 60 is provided so as to cover the leading end portion of the optical fiber 18, absorbs the light emitted from the optical fiber 18, and generates photoacoustic waves. The photoacoustic wave generation portion 60 is made of a material including a light absorber that absorbs light guided by the optical fiber 18 and a resin containing the light absorber. An example of the material forming the photoacoustic wave generation portion 60 is a synthetic resin, such as an epoxy resin, a fluorine resin, a silicone resin, an acrylic resin, or a polyurethane resin mixed with a black pigment that absorbs light. In addition, carbon black or titanium black, such as titanium oxide (TiO), may be mixed with the synthetic resin. Further, for example, an ultraviolet-curable resin, a thermosetting resin, or a photocurable resin can be used as the synthetic resin. The photoacoustic wave generation portion 60 is fixed to the inner wall of the needle tube 15a by the adhesion of the ultraviolet-curable resin, the thermosetting resin, or the photocurable resin together with the leading end portion of the optical fiber 18. In FIG. 2, the photoacoustic wave generation portion 60 is drawn with a larger size than the optical fiber 18. However, the invention is not limited thereto. The diameter of the photoacoustic wave generation portion 60 may be equal to the diameter of the optical fiber 18.

In the puncture needle 15 illustrated in FIG. 2, the leading end, that is, the light emission end of the optical fiber 18 needs not to protrude from the leading end opening 15b of the puncture needle 15. In the actual arrangement, it is desirable that the leading end of the optical fiber 18 is disposed as close to the leading end of the puncture needle 15 as possible in the range in which the leading end does not protrude from the leading end opening 15b of the puncture needle 15. Therefore, it is preferable that the leading end of the optical fiber 18 is disposed on the long inner surface, that is, the lower inner surface of the hollow portion 15c of the needle tube 15a. In addition, since the leading end portion of the optical fiber 18 is fixed to the inner surface of the needle tube 15a by the photoacoustic wave generation portion 60, the optical fiber 18 may be inserted into the hollow portion 15c of the needle tube 15a so as to be pressed against the lower inner surface, without coming off the lower inner surface, in order to easily fix the optical fiber 18 to the inner surface.

In order to control the insertion direction of the optical fiber 18 such that the leading end of the optical fiber 18 is pressed against the lower inner surface of the needle tube 15a in a case in which the optical fiber 18 is inserted into the hollow portion 15c of the needle tube 15a, it is necessary to set a contact point or a fixing point in the vicinity of an insertion opening for the optical fiber 18 in the chamber 16f of the needle base 16, that is, in the vicinity of the outlet of the outlet path 17b of the light introduction portion 17 and a contact point in the vicinity of the outlet of the optical fiber 18, that is, in the vicinity of the first chamber 16c in consideration of the straightening force of the optical fiber 18. In this case, the direction in which the optical fiber 18 is naturally inserted into the hollow portion 15c is determined.

In this embodiment, the optical fiber 18 is inserted from the inlet path 17c of the insertion path 17a to the third chamber 16e through the outlet path 17b. Here, since the outlet path 17b is formed with a smaller diameter than the inlet path 17c in order to define the insertion direction of the optical fiber 18, the movement of the optical fiber 18 is restricted in the outlet path 17b. Therefore, in this embodiment, the outlet of the outlet path 17b, that is, the chamber-side opening of the insertion path 17a is a first constraint point Y.

The optical fiber 18 is constrained at the first constraint point Y and then becomes free in the third chamber 16e. Then, the optical fiber 18 is bent toward the hollow portion 15c of the needle tube 15a and sequentially passes through the second chamber 16d and the first chamber 16c. Then, the optical fiber 18 is inserted into the hollow portion 15c of the needle tube 15a. In a case in which the optical fiber 18 is inserted from the second chamber 16d to the first chamber 16c, it comes into contact with the inner wall of the interface between the second chamber 16d and the first chamber 16c. Therefore, the contact point is a second constraint point X.

Here, a point where an extension line in the insertion direction of the optical fiber 18, that is, an axis line of the insertion path 17a in the vicinity of the chamber-side opening of the insertion path 17a of the light introduction portion 17 intersects a line that passes through the second constraint point X and is parallel to the axial direction of the needle tube 15a is an intersection point A. In a case in which the distance between the intersection point A and the second constraint point X is a distance a and the distance between the first constraint point Y and the intersection point A is a distance b, the chamber 16f is set such that the distance a is longer than the distance b, that is, a>b is satisfied in the invention.

In general, the force that makes the distance of the optical fiber 18 located in a section corresponding to the distance a equal to the distance of the optical fiber located in a section corresponding to the distance b acts due to the straightening force of the optical fiber 18, that is, repulsive force. That is, in the actual trajectory of the optical fiber 18 passing through the chamber 16f, the vertex of a convex portion in a case in which the optical fiber 18 is bent as described above is located in the vicinity of the point where a=b is established. In the invention, a>b is satisfied to match the length of the optical fiber 18 in the section corresponding to the distance b with the distance of the optical fiber 18 in the section corresponding to the distance a. Therefore, as represented by a thick line in FIG. 2, the vertex is located ahead of the intersection point A on the extension line in the insertion direction of the optical fiber 18.

The optical fiber 18 is inserted from the point that is located ahead of the intersection point A on the extension line in the insertion direction of the optical fiber 18 to the hollow portion 15c of the needle tube 15a through the second constraint point X. Therefore, as illustrated in FIG. 2, the optical fiber 18 is inserted into the hollow portion 15c from the upper side of the second constraint point X. Therefore, the optical fiber 18 is inserted from the upper side to the lower side in the hollow portion 15c of the needle tube 15a and the leading end of the optical fiber 18 is pressed against the lower inner wall, that is, the long inner wall of the hollow portion 15c, which makes it easy to fix the optical fiber 18 to the lower inner wall of the needle tube 15a. In a case in which the leading end of the optical fiber 18 is fixed by the photoacoustic wave generation portion 60, it is difficult for the optical fiber 18 to come off the inner surface of the hollow portion 15c.

For the distance a and the distance b, a:b=3:2 is preferable and a:b=3:1 is more preferable since the optical fiber 18 can be reliably pressed against the lower inner wall of the hollow portion 15c. However, the invention is not limited to this value. It is possible to obtain the above-mentioned effect in a case in which the distance a is slightly longer than the distance b.

Figure 14:
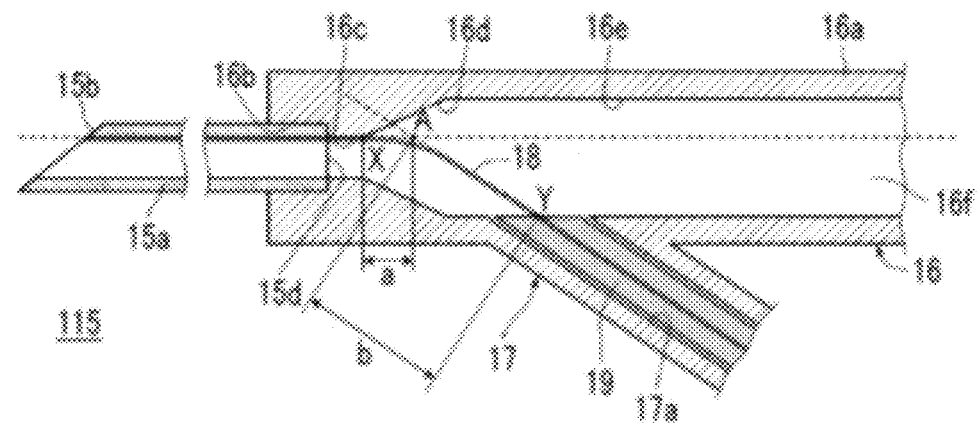
FIG. 14 is a cross-sectional view illustrating the configuration of a leading end portion of a puncture needle according to Comparative Example 1.

FIG. 14 is a cross-sectional view illustrating the configuration of a leading end portion of a puncture needle 115 as a comparative example of the puncture needle 15 according to the above-described embodiment. In general, it is desirable that the size of the needle base 16 in the longitudinal direction is small. Therefore, in the needle base 16, the light introduction portion 17 is located close to the needle tube 15a to reduce the distance a. As illustrated in FIG. 14, in a case in which the chamber 16f is set such that a<b is satisfied, the force that makes the length of the optical fiber 18 located in the section corresponding to the distance a equal to the length of the optical fiber located in the section corresponding to the distance b acts due to the straightening force of the optical fiber 18, that is, repulsive force. That is, in the actual trajectory of the optical fiber 18 passing through the chamber 16f, the vertex of a convex portion in a case in which the optical fiber 18 is bent as described above is located in the vicinity of the point where a=b is established. Therefore, as represented by a thick line in FIG. 14, the vertex is located at a position that is closer to the insertion path 17a than the intersection point A on the extension line in the insertion direction of the optical fiber 18, that is, on the lower side of the intersection point A.

The optical fiber 18 is inserted from the point that is located below the intersection point A on the extension line in the insertion direction of the optical fiber 18 to the hollow portion 15c of the needle tube 15a through the second constraint point X. Therefore, as illustrated in FIG. 14, the optical fiber 18 is inserted from the position below the second constraint point X to the hollow portion 15c. The optical fiber 18 is inserted from the lower side to the upper side in the hollow portion 15c of the needle tube 15a. The leading end of the optical fiber 18 is pressed against the upper inner surface, that is, the short inner surface of the hollow portion 15c. The leading end of the optical fiber 18 is likely to protrude from the leading end opening 15b of the needle tube 15a. In a case in which the leading end of the optical fiber 18 is fixed to the lower inner surface, that is, the long inner surface of the hollow portion 15c, it is difficult to fix the leading end of the optical fiber 18 and the optical fiber 18 is likely to come off after the leading end is fixed.

However, according to the puncture needle 15 of this embodiment, as described above, since the chamber 16f is set such that a>b is satisfied, the optical fiber 18 is inserted from the upper side to the lower side in the hollow portion 15c of the needle tube 15a and the leading end of the optical fiber 18 is pressed against the lower inner surface, that is, the long inner surface of the hollow portion 15c. Therefore, it is easy to fix the optical fiber 18 to the lower inner surface of the needle tube 15a. In a case in which the leading end of the optical fiber 18 is fixed by the photoacoustic wave generation portion 60, it is difficult for the optical fiber 18 to come off the inner surface of the hollow portion 15c.

Returning to FIG. 1, the ultrasound probe 11 corresponds to an acoustic wave detection unit according to the invention and includes, for example, a plurality of detector elements (ultrasound transducers) which are one-dimensionally arranged. The ultrasound probe 11 detects the photoacoustic waves generated from the photoacoustic wave generation portion 60 after the puncture needle 15 is inserted into the subject. The ultrasound probe 11 performs the transmission of acoustic waves (ultrasonic waves) to the subject and the reception of reflected acoustic waves (reflected ultrasonic waves) with respect to the transmitted ultrasonic waves, in addition to the detection of the photoacoustic waves. The transmission and reception of the ultrasonic waves may be performed at different positions. For example, ultrasonic waves may be transmitted from a position different from the position of the ultrasound probe 11 and the ultrasound probe 11 may receive the reflected ultrasonic waves with respect to the transmitted ultrasonic waves. For example, a linear ultrasound probe, a convex ultrasound probe, or a sector ultrasound probe can be used as the ultrasound probe 11. In addition, a two-dimensional array may be used.

The ultrasound unit 12 includes a receiving circuit 21, a receiving memory 22, a data demultiplexing unit 23, a photoacoustic image generation unit 24, an ultrasound image generation unit 25, an image output unit 26, a transmission control circuit 27, and a control unit 28. The ultrasound unit 12 typically includes, for example, a processor, a memory, and a bus. A program related to the generation of a photoacoustic image and the generation of an ultrasound image is incorporated into the memory of the ultrasound unit 12. The program is executed by the control unit 28 which is formed by a processor to implement the functions of the data demultiplexing unit 23, the photoacoustic image generation unit 24, the ultrasound image generation unit 25, and the image output unit 26. That is, each of these units is formed by the processor and the memory into which the program has been incorporated.

In this embodiment, the processor executes the program to implement the functions of each unit. However, the invention is not limited thereto and some or all of the functions may be implemented by hardware. The hardware configuration is not particularly limited and can be implemented by an appropriate combination of, for example, a plurality of integrated circuits (ICs), an application specific integrated circuit (ASIC), a field-programmable gate array (FPGA), a memory, and a circuit including a discrete component.

The receiving circuit 21 receives a detection signal output from the ultrasound probe 11 and stores the received detection signal in the receiving memory 22. The receiving circuit 21 typically includes a low-noise amplifier, a variable-gain amplifier, a low-pass filter, and an analog-to-digital converter (AD converter). The detection signal of the ultrasound probe 11 is amplified by the low noise amplifier. Then, gain adjustment corresponding to a depth is performed by the variable-gain amplifier and a high-frequency component of the detection signal is cut by the low-pass filter. Then, the detection signal is converted into a digital signal by the AD converter and the digital signal is stored in the receiving memory 22. The receiving circuit 21 is formed by, for example, one integral circuit (IC).

The ultrasound probe 11 outputs a detection signal of the photoacoustic waves and a detection signal of the reflected ultrasonic waves. The AD-converted detection signals (sampling data) of the photoacoustic waves and the reflected ultrasonic waves are stored in the receiving memory 22. The data demultiplexing unit 23 reads the sampling data of the detection signal of the photoacoustic waves from the receiving memory 22 and transmits the sampling data to the photoacoustic image generation unit 24. In addition, the data demultiplexing unit 23 reads the sampling data of the reflected ultrasonic waves from the receiving memory 22 and transmits the sampling data to the ultrasound image generation unit 25.

The photoacoustic image generation unit 24 generates a photoacoustic image on the basis of the detection signal of the photoacoustic waves detected by the ultrasound probe 11. The generation of the photoacoustic image includes, for example, image reconfiguration, such as phasing addition, detection, and logarithmic conversion. The ultrasound image generation unit 25 generates an ultrasound image (reflected acoustic image) on the basis of the detection signal of the reflected ultrasonic waves detected by the ultrasound probe 11. The generation of the ultrasound image includes, for example, image reconfiguration, such as phasing addition, detection, and logarithmic conversion. The image output unit 26 outputs the photoacoustic image and the ultrasound image to an image display unit 30 such as a display device.

The control unit 28 controls each component in the ultrasound unit 12. For example, in a case in which a photoacoustic image is acquired, the control unit 28 transmits a trigger signal to the laser unit 13 such that the laser unit 13 emits laser light. In addition, the control unit 28 transmits a sampling trigger signal to the receiving circuit 21 to control, for example, the sampling start time of the photoacoustic waves with the emission of the laser light.

In a case in which an ultrasound image is acquired, the control unit 28 transmits an ultrasound transmission trigger signal for commanding the transmission of ultrasonic waves to the transmission control circuit 27. In a case in which the ultrasound transmission trigger signal is received, the transmission control circuit 27 directs the ultrasound probe 11 to transmit ultrasonic waves. For example, the ultrasound probe 11 performs scanning while shifting acoustic lines one by one to detect the reflected ultrasonic waves. The control unit 28 transmits a sampling trigger signal to the receiving circuit 21 according to an ultrasound transmission time to start the sampling of the reflected ultrasonic waves.

Next, the operation of the photoacoustic measurement device 10 according to this embodiment will be described. First, a photoacoustic image generation process will be described with reference to a flowchart illustrated in FIG. 3.

In the photoacoustic image generation process, image acquisition conditions, such as a frame rate, the number of laser emission operations per frame, and the balance between the numbers of frames of reflected acoustic signals and photoacoustic image signals per frame, are stored in the memory (not illustrated) of the ultrasound unit 12 in advance. In addition, the control unit 28 determines light source driving conditions, such as a laser emission time, the number of laser pulses, and a current, so as to correspond to the image acquisition conditions and uses the light source driving conditions to drive the laser unit 13.

The photoacoustic image generation process starts in a state in which the connector 72 of the optical cable 70 connected to the puncture needle 15 is connected to the laser unit 13. The control unit 28 of the ultrasound unit 12 transmits a trigger signal to the laser unit 13. In a case in which the trigger signal is received, the laser unit 13 starts laser oscillation and emits pulsed laser light (S10). The pulsed laser light emitted from the laser unit 13 is guided by the optical cable 70 and is incident on the optical fiber 18 of the puncture needle 15. Then, the pulsed laser light is guided to the vicinity of the leading end of the puncture needle 15 by the optical fiber 18 in the puncture needle 15 and is emitted to the photoacoustic wave generation portion 60. The photoacoustic wave generation portion 60 absorbs the pulsed laser light and generates photoacoustic waves (S12). In addition, in the photoacoustic image generation process, a user, such as a doctor, inserts the puncture needle 15 into the subject at any time such as before or after the driving of the laser unit 13.

The ultrasound probe 11 detects the photoacoustic waves generated from the photoacoustic wave generation portion 60 irradiated with the laser light (S14). A detection signal of the photoacoustic waves output from the ultrasound probe 11 is received by the receiving circuit 21 and the sampling data of the detection signal is stored in the receiving memory 22. The photoacoustic image generation unit 24 receives the sampling data of the detection signal of the photoacoustic waves through the data demultiplexing unit 23 and generates a photoacoustic image (S16). The photoacoustic image generation unit 24 may apply a color map to convert signal intensity in the photoacoustic image into a color. The photoacoustic image generated by the photoacoustic image generation unit 24 is input to the image output unit 26 and the image output unit 26 displays the photoacoustic image on the image display unit 30 (S18).

Next, an ultrasound image generation process will be described with reference to a flowchart illustrated in FIG. 4. First, the control unit 28 transmits an ultrasound transmission trigger signal to the transmission control circuit 27 and the transmission control circuit 27 directs the ultrasound probe 11 to transmit ultrasonic waves in response to the ultrasound transmission trigger signal (S30). The ultrasound probe 11 transmits ultrasonic waves and then detects reflected ultrasonic waves (S32). Then, a detection signal of the reflected ultrasonic waves is received by the receiving circuit 21 and the sampling data of the detection signal is stored in the receiving memory 22. The ultrasound image generation unit 25 receives the sampling data of the detection signal of the ultrasonic waves through the data demultiplexing unit 23 and generates an ultrasound image (S34). The ultrasound image generation unit 25 may apply a color map to convert signal intensity in the ultrasound image into a color. The ultrasound image generated by the ultrasound image generation unit 25 is input to the image output unit 26 and the image output unit 26 displays the ultrasound image on the image display unit 30 (S36).

The image display unit 30 may display a composite image of the photoacoustic image and the ultrasound image. In this case, it is possible to check the position of the leading end of the puncture needle 15 in a living body and thus to accurately perform a safe needling operation.

Next, puncture needles 15 using other embodiments of the insert according to the invention will be described.

Figure 5:
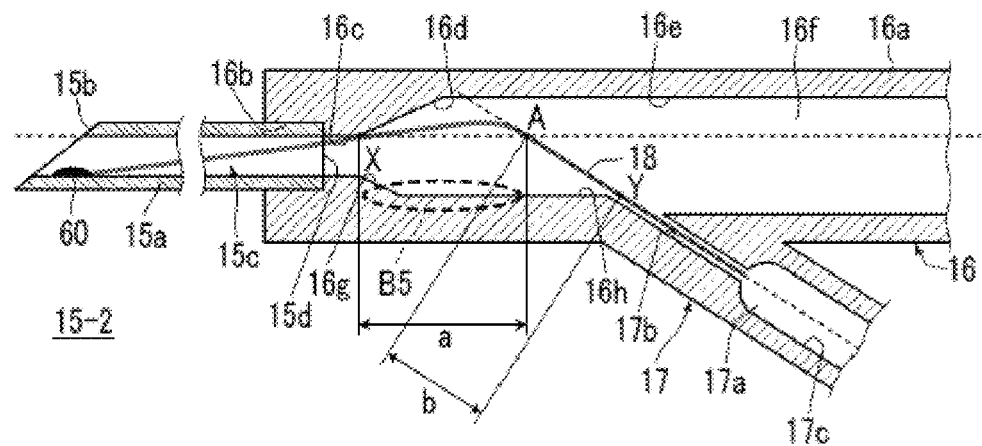
FIG. 5 is a cross-sectional view illustrating the configuration of a leading end portion of a puncture needle according to a second embodiment.

First, a puncture needle 15-2 according to a second embodiment of the invention will be described. FIG. 5 is a cross-sectional view illustrating the configuration of a leading end portion of the puncture needle 15-2 according to the second embodiment provided with the optical fiber 18. In the puncture needle 15-2 according to this embodiment, the same configurations as those in the puncture needle 15 according to the first embodiment illustrated in FIG. 1 are denoted by the same reference numerals and the description thereof will not be repeated. Only different portions will be described.

As described above, in general, it is desirable that the size of the needle base 16 in the longitudinal direction is small from the viewpoint of cost and operability. Therefore, in the puncture needle 15-2 according to this embodiment, as represented by a dotted line B5 in FIG. 5, a lower wall 16h of the chamber 16f which is close to the needle tube 15a from the outlet path 17b, that is, the chamber-side opening of the light introduction portion 17 in the chamber 16f is high. That is, the lower wall 16h of the chamber 16f which is on the leading end side from the chamber-side opening has a shape which extends from the chamber-side opening along an extension line of the lower wall of the insertion path 17a and is bent below the extension line. On a line that is orthogonal to the axis of the needle tube 15a at a bent point where the lower wall is bent, the distance from the bent point to the axis of the needle tube 15a is shorter than the distance from the upper wall of the chamber 16f to the axis of the needle tube 15a. In this embodiment, the bent point is the first constraint point Y. In addition, the distance of a lower inclined surface 16g of the second chamber 16d in the longitudinal direction is short and the shapes of the upper and lower surfaces of the chamber 16f which face each other with the axis of the needle base 16 interposed therebetween are asymmetric.

In this configuration, since the position of the first constraint point Y is closer to the intersection point A than that in the puncture needle 15 according to the first embodiment, the distance b is short. Therefore, the distance a can be set to a small value.

Figure 6:
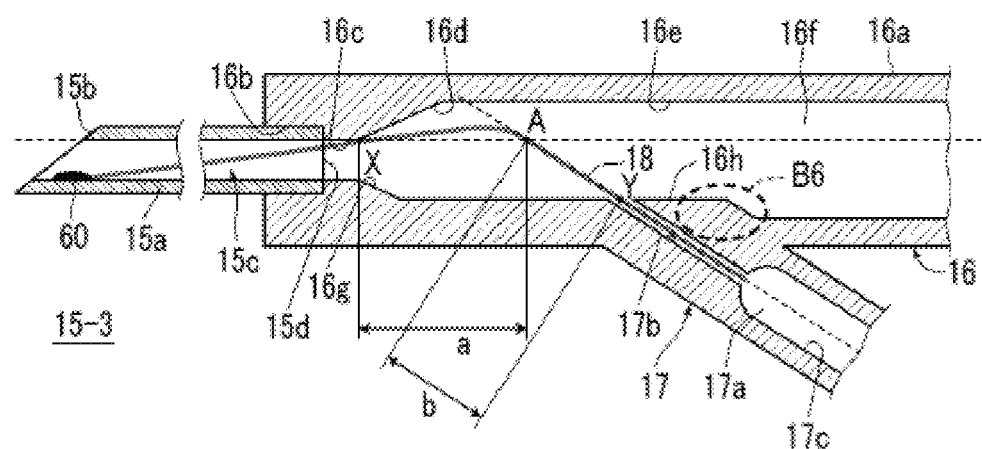
FIG. 6 is a cross-sectional view illustrating the configuration of a leading end portion of a puncture needle according to a third embodiment.

Next, a puncture needle 15-3 according to a third embodiment of the invention will be described. FIG. 6 is a cross-sectional view illustrating the configuration of a leading end portion of the puncture needle 15-3 according to the third embodiment provided with the optical fiber 18. In the puncture needle 15-3 according to this embodiment, the same configurations as those in the puncture needle 15-2 according to the second embodiment illustrated in FIG. 5 are denoted by the same reference numerals and the description thereof will not be repeated. Only different portions will be described.

In the puncture needle 15-3 according to this embodiment, as represented by a dotted line B6 in FIG. 6, in addition to the configuration of the puncture needle 15-2 according to the second embodiment, the lower wall 16h of the chamber 16f including at least a portion of the lower wall of the third chamber 16e which is on the rear end side of the needle base 16 from the outlet path 17b of the light introduction portion 17 in the chamber 16f is high. That is, the entire lower wall 16h of the chamber 16f forming the outlet path 17b is high. In this configuration, since the length of the outlet path 17b in the axial direction is longer than that in the puncture needle 15-2 according to the second embodiment, it is possible to increase adhesive force in a case in which the outlet path 17b is filled with, for example, an adhesive for fixing the optical fiber 18. In a case in which the adhesion length of the optical fiber 18 is the same, it is possible to reduce the length of the light introduction portion 17 protruding from the needle base main body 16a. Therefore, the light introduction portion 17 does not get in the way.

Figure 7:
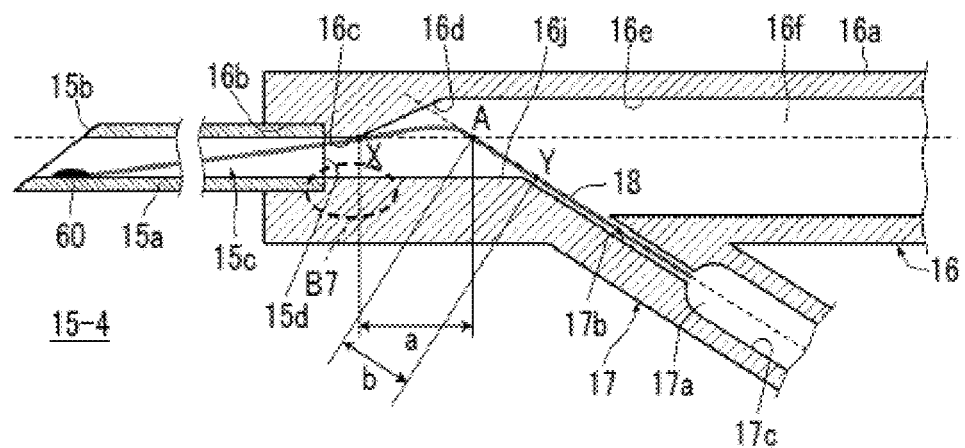
FIG. 7 is a cross-sectional view illustrating the configuration of a leading end portion of a puncture needle according to a fourth embodiment.

Next, a puncture needle 15-4 according to a fourth embodiment of the invention will be described. FIG. 7 is a cross-sectional view illustrating the configuration of a leading end portion of the puncture needle 15-4 according to the fourth embodiment provided with the optical fiber 18. In the puncture needle 15-4 according to this embodiment, the same configurations as those in the puncture needle 15-2 according to the second embodiment illustrated in FIG. 5 are denoted by the same reference numerals and the description thereof will not be repeated. Only different portions will be described.

In the puncture needle 15-4 according to this embodiment, as represented by a dotted line B7 in FIG. 7, in addition to the configuration of the puncture needle 15-2 according to the second embodiment, at least a portion of the third chamber 16e which is on the side of the needle tube 15a from the outlet path 17b of the light introduction portion 17 and the second chamber 16d communicating with the third chamber 16e in the chamber 16f is high and the height of at least a portion of the second chamber 16d and the third chamber 16e below the axis of the needle base 16 is equal to the height of the first chamber 16c as illustrated in FIG. 7. That is, the lower wall 16j of the chamber which is on the leading end side from the chamber-side opening of the insertion path 17a has a shape which extends from the chamber-side opening along the extension line of the lower wall of the insertion path 17a and is bent below the extension line and the lower wall 16j is formed so as to have the same height as the lower surface of the hollow portion 15c of the needle tube 15a through a bent point where the lower wall 16j is bent. In this embodiment, the bent point is the first constraint point Y.

In this configuration, since the position of the first constraint point Y is further closer to the intersection point A than that in the puncture needles 15, 15-2, and 15-3 according to the first to third embodiments, the distance b is further reduced. Therefore, the distance a can be set to be further reduced.

Figure 8:
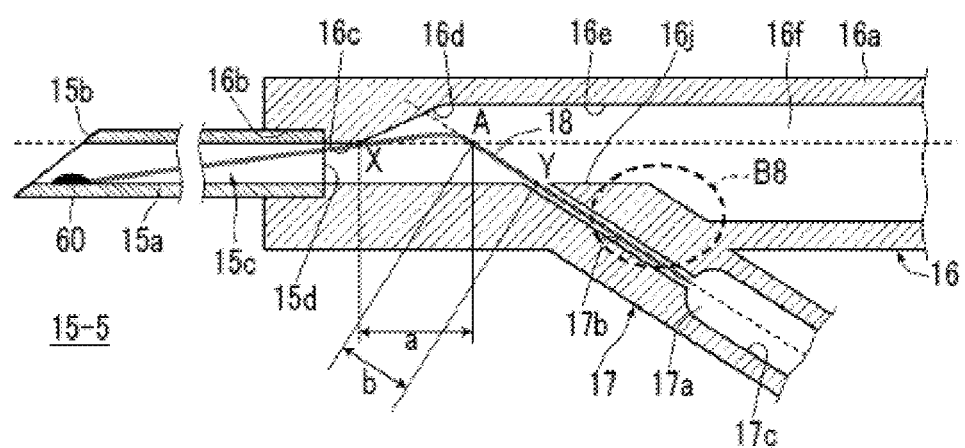
FIG. 8 is a cross-sectional view illustrating the configuration of a leading end portion of a puncture needle according to a fifth embodiment.

Next, a puncture needle 15-5 according to a fifth embodiment of the invention will be described. FIG. 8 is a cross-sectional view illustrating the configuration of a leading end portion of the puncture needle 15-5 according to the fifth embodiment provided with the optical fiber 18. In the puncture needle 15-5 according to this embodiment, the same configurations as those in the puncture needle 15-4 according to the fourth embodiment illustrated in FIG. 7 are denoted by the same reference numerals and the description thereof will not be repeated. Only different portions will be described.

In the puncture needle 15-5 according to this embodiment, as represented by a dotted line B8 in FIG. 8, in addition to the configuration of the puncture needle 15-4 according to the fourth embodiment, the lower wall 16j of the chamber 16f including at least a portion of the lower wall of the third chamber 16e which is on the rear end side of the needle base 16 from the outlet path 17b of the light introduction portion 17 in the chamber 16f is high. That is, the entire lower wall 16j of the chamber 16f forming the outlet path 17b is high. In this configuration, since the length of the outlet path 17b in the axial direction is further larger than that in the puncture needle 15-3 according to the third embodiment, it is possible to further increase adhesive force in a case in which the outlet path 17b is filled with, for example, an adhesive for fixing the optical fiber 18. In a case in which the adhesion length of the optical fiber 18 is the same, it is possible to further reduce the length of the light introduction portion 17 protruding from the needle base main body 16a. Therefore, the light introduction portion 17 does not get in the way.

Figure 9:
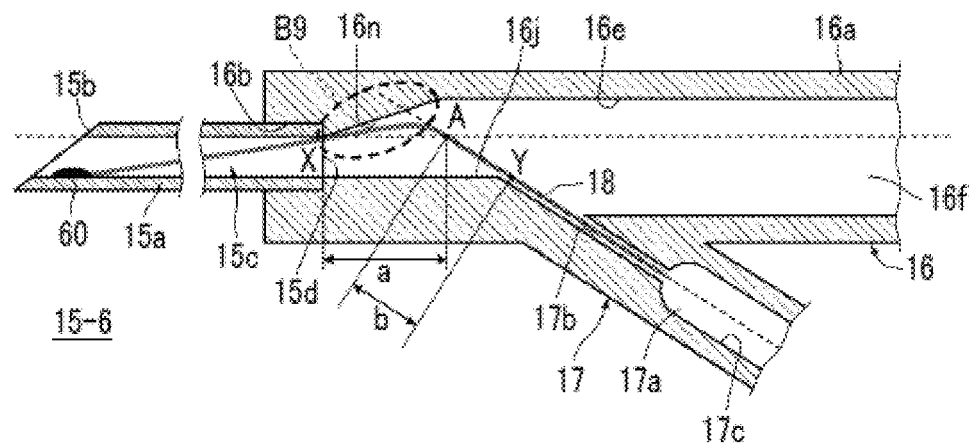
FIG. 9 is a cross-sectional view illustrating the configuration of a leading end portion of a puncture needle according to a sixth embodiment.

Next, a puncture needle 15-6 according to a sixth embodiment of the invention will be described. FIG. 9 is a cross-sectional view illustrating the configuration of a leading end portion of the puncture needle 15-6 according to the sixth embodiment provided with the optical fiber 18. In the puncture needle 15-6 according to this embodiment, the same configurations as those in the puncture needle 15-4 according to the fourth embodiment illustrated in FIG. 7 are denoted by the same reference numerals and the description thereof will not be repeated. Only different portions will be described.

In the puncture needle 15-6 according to this embodiment, as represented by a dotted line B9 in FIG. 9, in addition to the configuration of the puncture needle 15-4 according to the fourth embodiment, an upper wall 16n of the chamber 16f is formed such that the height thereof gradually increases backward from the opening of the chamber 16f close to the needle tube 15a to the rear end of the second chamber 16d. That is, the upper wall 16n of the first chamber 16c is inclined and tapered from the needle tube 15a to the rear end of the second chamber 16d.

In this configuration, the position of the first constraint point Y is disposed at the boundary between the leading end of the chamber 16f and the needle tube 15a. Since the position of the first constraint point Y is moved to the leading end, the distance a can be set to a large value.

Figure 10:
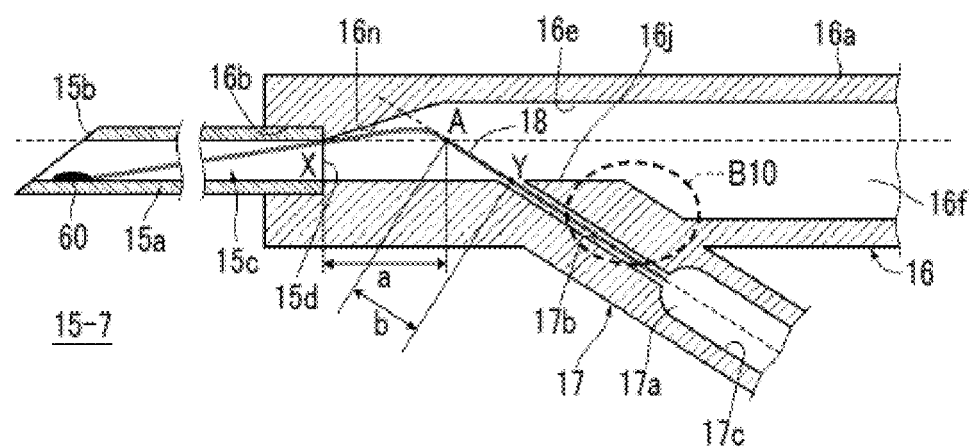
FIG. 10 is a cross-sectional view illustrating the configuration of a leading end portion of a puncture needle according to a seventh embodiment.

Next, a puncture needle 15-7 according to a seventh embodiment of the invention will be described. FIG. 10 is a cross-sectional view illustrating the configuration of a leading end portion of the puncture needle 15-7 according to the seventh embodiment provided with the optical fiber 18. In the puncture needle 15-7 according to this embodiment, the same configurations as those in the puncture needle 15-6 according to the sixth embodiment illustrated in FIG. 9 are denoted by the same reference numerals and the description thereof will not be repeated. Only different portions will be described.

In the puncture needle 15-7 according to this embodiment, as represented by a dotted line B10 in FIG. 10, in addition to the configuration of the puncture needle 15-6 according to the sixth embodiment, the lower wall 16j of the chamber 16f including at least a portion of the lower wall of the third chamber 16e which is on the rear end side of the needle base 16 from the outlet path 17b of the light introduction portion 17 in the chamber 16f is high. That is, the entire lower wall 16j of the chamber 16f forming the outlet path 17b is high. In this configuration, since the length of the outlet path 17b in the axial direction is further larger than that in the puncture needle 15-3 according to the third embodiment, it is possible to further increase adhesive force in a case in which the outlet path 17b is filled with, for example, an adhesive for fixing the optical fiber 18. In a case in which the adhesion length of the optical fiber 18 is the same, it is possible to further reduce the length of the light introduction portion 17 protruding from the needle base main body 16a. Therefore, the light introduction portion 17 does not get in the way.

Figure 11:
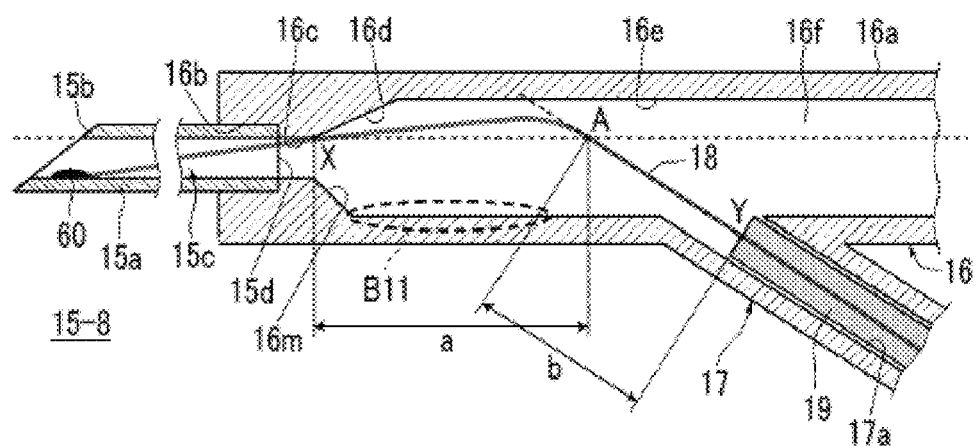
FIG. 11 is a cross-sectional view illustrating the configuration of a leading end portion of a puncture needle according to an eighth embodiment.

Next, a puncture needle 15-8 according to an eighth embodiment of the invention will be described. FIG. 11 is a cross-sectional view illustrating the configuration of a leading end portion of the puncture needle 15-8 according to the eighth embodiment provided with the optical fiber 18. In the puncture needle 15-8 according to this embodiment, the same configurations as those in the puncture needle 15 according to the first embodiment illustrated in FIG. 1 are denoted by the same reference numerals and the description thereof will not be repeated. Only different portions will be described.

As illustrated in FIG. 11, the puncture needle 15-8 according to this embodiment is formed such that the inside diameter of the insertion path 17a of the light introduction portion 17 is the same in the axial direction of the insertion path 17a and is larger than the inside diameter of the outlet path 17b of the insertion path 17a in the first embodiment, that is, is equal to the inside diameter of the inlet path 17c. In this embodiment, the insertion path 17a is filled with an adhesive in order to restrict the movement of the optical fiber 18 in the insertion path 17a. In this embodiment, as illustrated in FIG. 11, an end surface of the adhesive which is close to the chamber 16f is located in the insertion path 17a. The end surface of the adhesive close to the chamber 16f restricts the movement of the optical fiber 18. Therefore, the first constraint point Y is set on the end surface. That is, the optical fiber 18 does not come into contact with the lower inner surface of the chamber 16f while the optical fiber 18 is inserted into the hollow portion 15c of the needle tube 15a through the insertion path 17a.

In the above-mentioned configuration, the first constraint point Y is further away from the intersection point A than that in the puncture needle according to the first embodiment. As a result, the distance b becomes long. In a case in which the diameter of the insertion path 17a is large, the distance a is set to be sufficiently longer than that in the puncture needle 15 according to the first embodiment as represented by a dotted line B11 in FIG. 11, in order to prevent the optical fiber 18 from coming off the inner surface of the needle tube 15a. This configuration makes it possible to achieve a>b in the chamber 16f.

Figure 12:
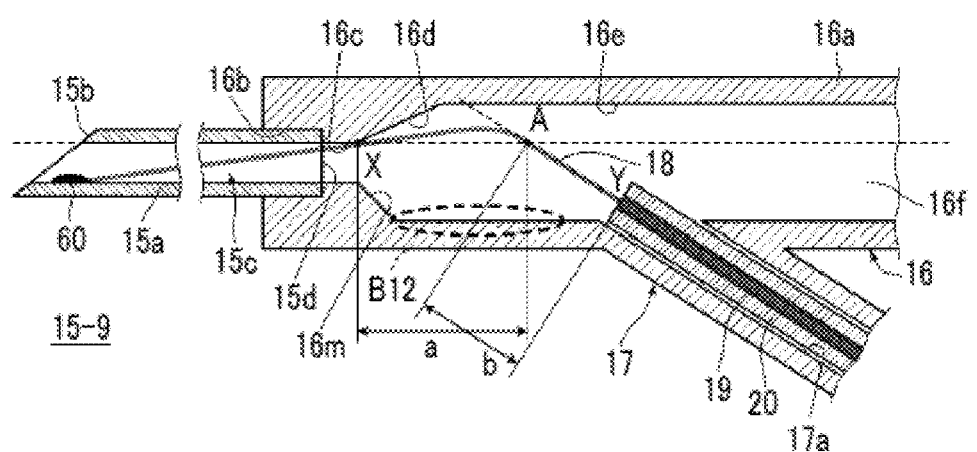
FIG. 12 is a cross-sectional view illustrating the configuration of a leading end portion of a puncture needle according to a ninth embodiment.

Next, a puncture needle 15-9 according to a ninth embodiment of the invention will be described. FIG. 12 is a cross-sectional view illustrating the configuration of a leading end portion of the puncture needle 15-9 according to the ninth embodiment provided with the optical fiber 18. In the puncture needle 15-9 according to this embodiment, the same configurations as those in the puncture needle 15-8 according to the eighth embodiment illustrated in FIG. 11 are denoted by the same reference numerals and the description thereof will not be repeated. Only different portions will be described.

As illustrated in FIG. 12, the puncture needle 15-9 according to this embodiment comprises a protective tube 20 that covers the optical fiber 18 and the optical fiber 18 covered with the protective tube 20 is inserted into the insertion path 17a. A space between the protective tube 20 and the optical fiber 18 is filled with the adhesive 19 and the first constraint point Y is located on an end surface of the adhesive 19 which is close to the chamber 16f. In this embodiment, the protective tube 20 is entirely filled with the adhesive in the longitudinal direction. However, the invention is not limited thereto. Only a portion of the opening which is close to the chamber 16f may be filled with an adhesive in order to prevent the inflow of, for example, liquid medicines from the chamber 16f.

In a case in which the inside diameter of the insertion path 17a is larger than the inside diameter of the outlet path 17b of the insertion path 17a according to the first embodiment as in this embodiment, the use of the protective tube 20 makes it possible to restrict the movement of the optical fiber 18 in the insertion path 17a. In addition, as illustrated in FIG. 12, the protective tube 20 is disposed such that at least a portion of the leading end of the protective tube 20 protrudes to the chamber 16f and the position of the first constraint point Y becomes close to the intersection point A. Therefore, the distance b is reduced. As a result, the distance a can be set to a small value.

Figure 13:
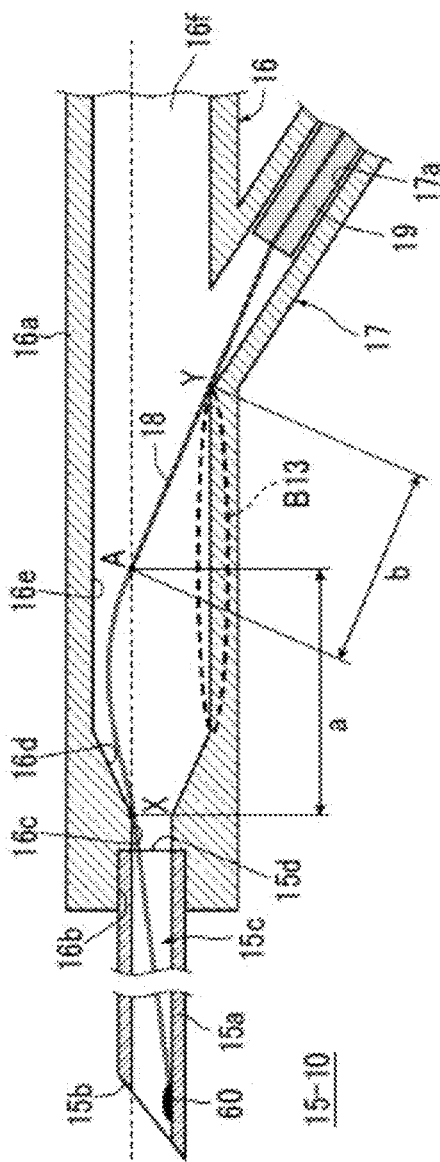
FIG. 13 is a cross-sectional view illustrating the configuration of a leading end portion of a puncture needle according to a tenth embodiment.

Next, a puncture needle 15-10 according to a tenth embodiment of the invention will be described. FIG. 13 is a cross-sectional view illustrating the configuration of a leading end portion of the puncture needle 15-10 according to the tenth embodiment provided with the optical fiber 18. In the puncture needle 15-10 according to this embodiment, the same configurations as those in the puncture needle 15-8 according to the eighth embodiment illustrated in FIG. 11 are denoted by the same reference numerals and the description thereof will not be repeated. Only different portions will be described.

In the puncture needle 15-10 according to this embodiment, as illustrated in FIG. 13, the insertion path 17a is filled with an adhesive in order to restrict the movement of the optical fiber 18 in the insertion path 17a. In this embodiment, as illustrated in FIG. 13, an end surface of the adhesive which is close to the chamber 16f is located in the insertion path 17a. The end surface of the adhesive close to the chamber 16f restricts the movement of the optical fiber 18. However, in a case in which the optical fiber 18 comes out of the end surface of the adhesive close to the chamber 16f, it is bent from the insertion direction of the insertion path 17a and comes into contact with the boundary between the needle base main body 16a and the light introduction portion 17. Therefore, the first constraint point Y is set as the contact point.

In the above-mentioned configuration, the first constraint point Y is further away from the intersection point A than that in the puncture needle according to the first embodiment. As a result, the distance b becomes long. In a case in which the diameter of the insertion path 17a is large, the distance a is set to be sufficiently longer than that in the puncture needle 15 according to the first embodiment as represented by a dotted line B13 in FIG. 13, in order to prevent the optical fiber 18 from coming off the inner surface of the needle tube 15a. This configuration makes it possible to achieve a>b in the chamber 16f.

Figure 15:
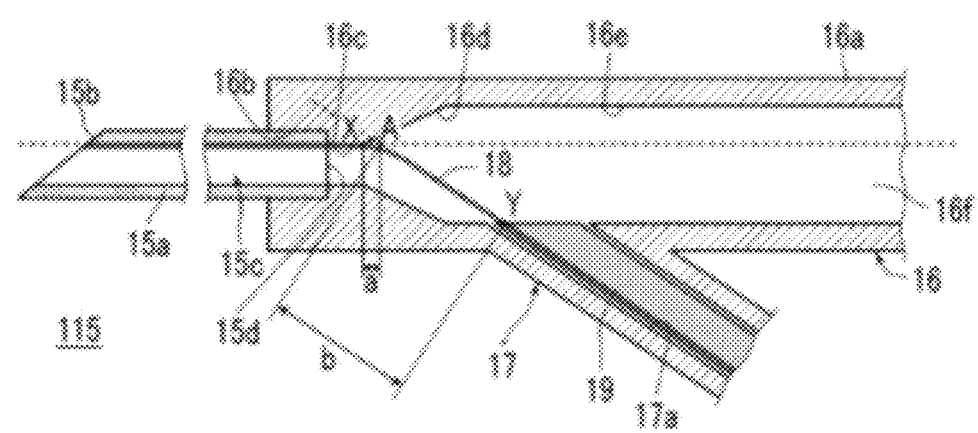
FIG. 15 is a cross-sectional view illustrating the configuration of a leading end portion of a puncture needle according to Comparative Example 2.
Figure 16:
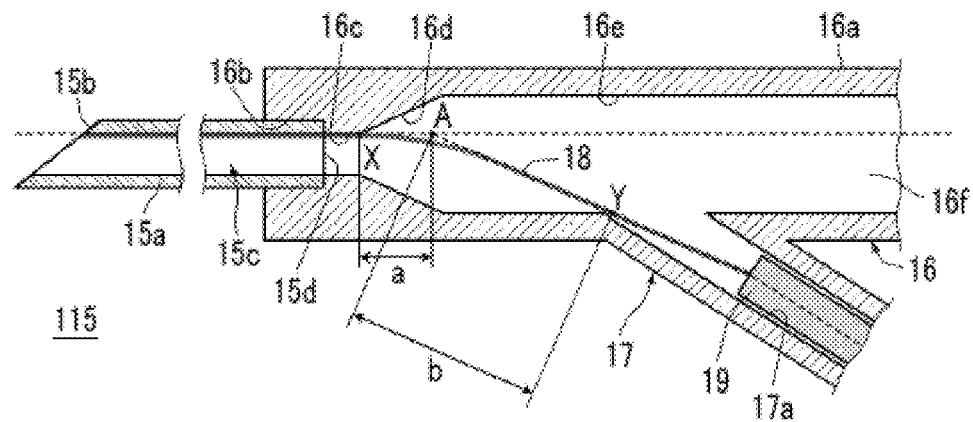
FIG. 16 is a cross-sectional view illustrating the configuration of a leading end portion of a puncture needle according to Comparative Example 3.
Figure 17:
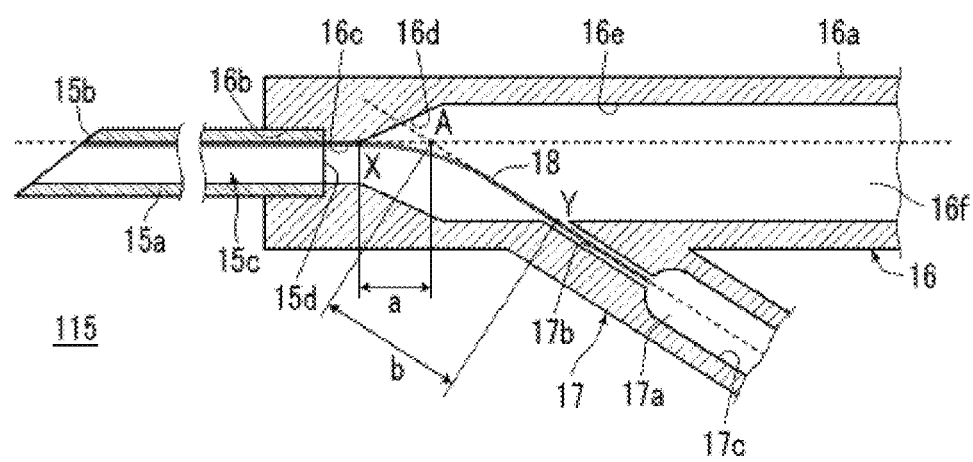
FIG. 17 is a cross-sectional view illustrating the configuration of a leading end portion of a puncture needle according to Comparative Example 4.

FIGS. 15 to 17 are cross-sectional views illustrating the configuration of a leading end portion of a puncture needle 115 as a comparative example of the puncture needles 15-8, 15-9, and 15-10 according to the eighth to tenth embodiments. In general, in a case in which the optical fiber 18 is inserted into the insertion path 17a of the light introduction portion 17, the insertion path 17a is filled with an adhesive up to the chamber 16f to fix the optical fiber 18.

It is desirable that the size of the needle base 16 in the longitudinal direction is small from the viewpoint of cost and operability. Therefore, the light introduction portion 17 is located so as to be close to the needle tube 15a in the needle base 16 to reduce the distance a. In FIG. 16, the optical fiber 18 is disposed along the axis of the insertion path 17a. In contrast, in FIG. 15, the optical fiber 18 is disposed along the lower inner surface of the insertion path 17a such that the distance a is shorter than that in the puncture needle 115 illustrated in FIG. 16. Even in a case in which the first constraint point Y is set at the boundary between the needle base main body 16a and the light introduction portion 17 as illustrated in FIG. 17 similarly to the tenth embodiment, the distance a is set to be shorter than the distance b.

In the puncture needles 15-8, 15-9, and 15-10 according to the eighth to tenth embodiments, even in a case in which the insertion direction and insertion position of the optical fiber 18 into the chamber 16f are changed as in the puncture needles 115 according to the comparative examples illustrated in FIGS. 15 to 17, for example, the length from the leading end opening of the chamber 16f to the light introduction portion 17, the position of the end surface of the adhesive close to the chamber 16f, the inside diameter of the protective tube 20, the position of the leading end of the protective tube 20, and the insertion angle of the optical fiber 18 are set such that a>b can be sufficiently satisfied.

In the above-described embodiments, the puncture needle 15 is considered as the insert. However, the invention is not limited thereto. The insert may be a radio-frequency ablation needle including an electrode that is used for radio-frequency ablation.

The insert according to the embodiment of the invention is not limited to a needle, such as an injection needle, and may be a biopsy needle used for biopsy. That is, the insert may be a biopsy needle that is inserted into an inspection target of the living body and extracts the tissues of a biopsy site of the inspection target. In this case, photoacoustic waves may be generated from an extraction portion (intake port) for sucking and extracting the tissues of the biopsy site. In addition, the needle may be used as a guiding needle that is used for insertion into a deep part, such as a part under the skin or an organ inside the abdomen. The insert may also be used as a needle that passes through an endoscope and comes out of the forceps port.

The invention has been described above on the basis of the preferred embodiments. However, the insert and the photoacoustic measurement device according to the embodiment of the invention are not limited only to the above-described embodiments. Various modifications and changes of the configurations according to the above-described embodiments are also included in the scope of the invention.

EXPLANATION OF REFERENCES

10: photoacoustic measurement device
11: ultrasound probe
12: ultrasound unit
13: laser unit
14: optical fiber
14a: light emission end
14b: side surface
15, 115: puncture needle
15a: needle tube
15b: leading end opening
15c: hollow portion
15d: rear end portion
16: needle base
16a: needle base main body
16b: anterior end portion
16c: first chamber
16d: second chamber
16e: third chamber
16f: chamber
16g: lower inclined surface
16h: lower wall
16j: lower wall
16n: upper wall
17: light introduction portion
17a: insertion path
17b: outlet path
17c: outlet path
18: optical fiber
19: adhesive
20: protective tube
21: receiving circuit
22: receiving memory
23: data demultiplexing unit
24: photoacoustic image generation unit
25: ultrasound image generation unit
26: image output unit
27: transmission control circuit
28: control unit
30: image display unit
60: photoacoustic wave generation portion
70: optical cable
72: connector
A: intersection point
Y: first constraint point
X: second constraint point

What is claimed is:

1. An insert of which at least a portion is inserted into a subject, the insert comprising:
   a hollow needle tube that has an inclined surface comprising a leading end opening at a leading end;
   a long needle base that has a chamber whose leading end communicates with an inside of the needle tube and holds a rear end portion of the needle tube; and
   a light introduction portion that communicates with the chamber and has an insertion path into which a light guide member guiding light emitted from a light source is inserted,
   wherein, in a cross section including an axis of the needle tube and an axis of the insertion path, in a case in which a direction from the axis of the needle tube to a side on which the light introduction portion is located is a downward direction and a direction opposite to the downward direction is an upward direction, the inclined surface faces upward, a chamber-side opening of the insertion path is formed in a lower wall of the chamber, and the insertion path obliquely extends backward from the chamber-side opening in the downward direction,
   an upper wall of the chamber which is on a leading end side from the chamber-side opening is formed such that a height thereof gradually increases from the leading end to a rear end, and
   in a case in which the light guide member is inserted into the insertion path, is constrained at a first constraint point Y, becomes free, is bent, is constrained at a second constraint point X, and is inserted into the needle tube and a point where an extension line in an insertion direction of the light guide member in the vicinity of the chamber-side opening in the insertion path intersects a line which passes through the second constraint point X and is parallel to an axial direction of the needle tube is an intersection point A, a distance a between the intersection point A and the second constraint point X is longer than a distance b between the first constraint point Y and the intersection point A.

2. The insert according to claim 1,
   wherein, in the cross section, a lower wall of the chamber which is on the leading end side from the chamber-side opening has a shape that extends from the chamber-side opening along an extension line of a lower wall of the insertion path and is bent below the extension line and a distance from a bent point where the lower wall is bent to the axis of the needle tube is shorter than a distance from the upper wall of the chamber to the axis of the needle tube on a line orthogonal to the axis of the needle tube at the bent point.

3. The insert according to claim 2,
wherein, in the cross section, the lower wall of the chamber which is on the leading end side from the chamber-side opening is formed with the same height as a lower surface of a hollow portion of the needle tube through the bent point.

4. The insert according to claim 1,
wherein, in the cross section, the upper wall of the chamber which is on the leading end side from the intersection point A is formed such that a height thereof gradually increases from a height position of an upper surface of the hollow portion of the needle tube to the rear.

5. An optical insert comprising:
the insert according to claim 1; and
the light guide member that is inserted into the insertion path, is constrained at the first constraint point Y, becomes free, is bent, is constrained at the second constraint point X, and is inserted into the needle tube.

6. The optical insert according to claim 5,
wherein a clearance between an inside diameter of a chamber-side portion of the insertion path and an outside diameter of the light guide member is equal to or less than 0.5 mm.

7. The optical insert according to claim 5,
wherein the light guide member is fixed in the insertion path by an adhesive.

8. The optical insert according to claim 5, further comprising:
a protective tube that covers the light guide member,
wherein the light guide member is fixed in the protective tube by an adhesive.

9. The optical insert according to claim 5, further comprising:
a photoacoustic wave generation portion that is provided at a light emission end of the light guide member which is disposed on the leading end side of the needle tube, absorbs light emitted from the light emission end, and generates photoacoustic waves.

10. The optical insert according to claim 9,
wherein the photoacoustic wave generation portion is made of an ultraviolet-curable resin including a pigment that absorbs light guided by the light guide member.

11. The optical insert according to claim 10,
wherein the ultraviolet-curable resin functions as an adhesive that fixes the photoacoustic wave generation portion to the needle tube.

12. A photoacoustic measurement device comprising:
the optical insert according to claim 9;
a light source unit that emits light which is absorbed by the photoacoustic wave generation portion of the optical insert; and
an acoustic wave detection unit that detects photoacoustic waves generated from the photoacoustic wave generation portion.

* * * * *